(12) United States Patent
Tamura et al.

(10) Patent No.: US 8,221,314 B2
(45) Date of Patent: Jul. 17, 2012

(54) CAPSULE TYPE ENDOSCOPE FOR SENDING DATA IN HUMAN BODY COMMUNICATION SYSTEM

(75) Inventors: Kazuaki Tamura, Hachioji (JP); Tetsuo Minai, Hachioji (JP); Jin Ohara, Hachioji (JP)

(73) Assignee: Olympus Corporation, Tokyo (JP)

( * ) Notice: Subject to any disclaimer, the term of this patent is extended or adjusted under 35 U.S.C. 154(b) by 1296 days.

(21) Appl. No.: 11/926,612

(22) Filed: Oct. 29, 2007

(65) Prior Publication Data
US 2008/0125623 A1 May 29, 2008

(30) Foreign Application Priority Data
Nov. 27, 2006 (JP) .................. 2006-319145

(51) Int. Cl.
*A61B 1/06* (2006.01)
*A61B 5/07* (2006.01)
*A61B 5/05* (2006.01)

(52) U.S. Cl. ............... 600/160; 600/302; 600/347

(58) Field of Classification Search .......... 600/160, 600/302, 111, 527, 595, 410, 547, 101, 347, 600/424, 118, 377, 12, 25, 30, 40, 29; 128/899, 128/920; 607/17, 60, 18, 27, 62; 604/93.01, 604/891.1
See application file for complete search history.

(56) References Cited

U.S. PATENT DOCUMENTS

| | | | | |
|---|---|---|---|---|
| 3,711,766 A | * | 1/1973 | Dahm | 324/209 |
| 2002/0193669 A1 | * | 12/2002 | Glukhovsky | 600/302 |
| 2005/0183733 A1 | * | 8/2005 | Kawano et al. | 128/899 |
| 2006/0173265 A1 | * | 8/2006 | Kim et al. | 600/407 |
| 2006/0243288 A1 | * | 11/2006 | Kim et al. | 128/899 |

FOREIGN PATENT DOCUMENTS

| | | |
|---|---|---|
| EP | 1 159 917 A1 | 12/2001 |
| JP | 2006-513001 | 4/2006 |
| JP | 2006-513670 | 4/2006 |
| JP | 2006-324774 | 11/2006 |
| WO | WO 2007/049845 A2 | 5/2007 |
| WO | WO 2007/148877 A1 | 12/2007 |
| WO | WO 2008/016194 A2 | 2/2008 |

OTHER PUBLICATIONS

Extended Supplementary European Search Report dated Sep. 28, 2010.

* cited by examiner

*Primary Examiner* — John P Leubecker
*Assistant Examiner* — Ronald D Colque
(74) *Attorney, Agent, or Firm* — Scully, Scott, Murphy & Presser, P.C.

(57) ABSTRACT

A capsule type endoscope which is introduced into a subject to acquire subject internal information and transmits the acquired subject internal information to the outside through the subject has a plurality of electrodes arranged on an outer peripheral surface thereof. An electrode selecting section selects two electrodes with a small transmission power loss from the plurality of electrodes as transmitting electrodes that are utilized to transmit the subject internal information. A transmitting section uses the two transmitting electrodes selected by the electrode selecting section to transmit the subject internal information to the outside of the subject.

3 Claims, 3 Drawing Sheets

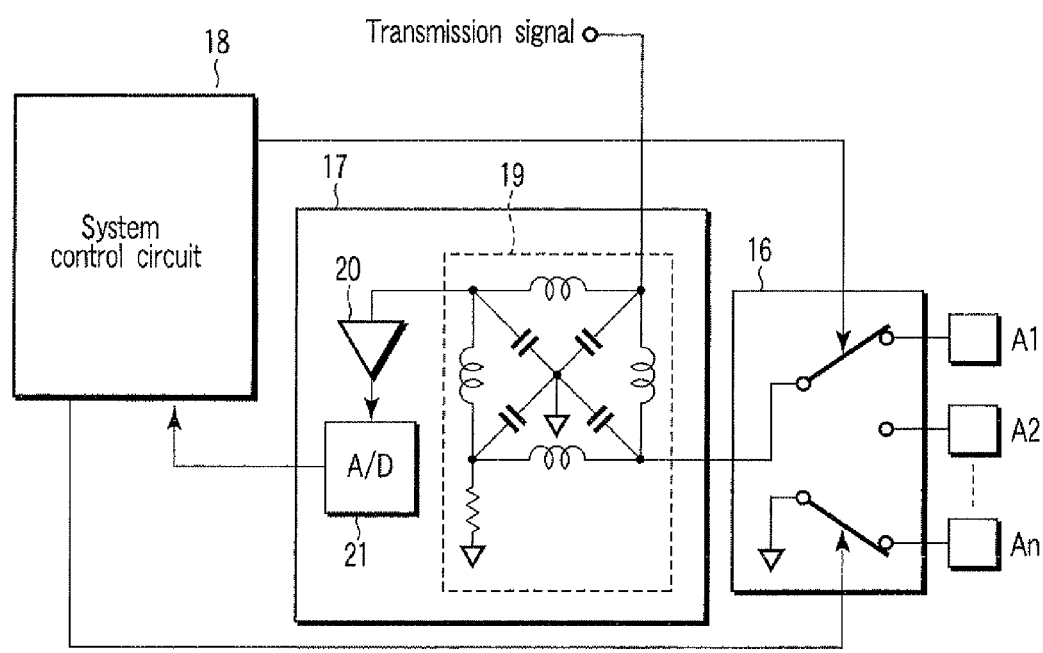
F I G. 5

CAPSULE TYPE ENDOSCOPE FOR SENDING DATA IN HUMAN BODY COMMUNICATION SYSTEM

CROSS-REFERENCE TO RELATED APPLICATIONS

This application is based upon and claims the benefit of priority from prior Japanese Patent Application No. 2006-319145, filed Nov. 27, 2006, the entire contents of which are incorporated herein by reference.

BACKGROUND OF THE INVENTION

1. Field of the Invention

The present invention relates to a capsule type endoscope that is introduced into a subject and transmits subject internal information to an external receiving device while moving in the subject with the subject being used as a signal transmission medium.

2. Description of the Related Art

Presently, in the endoscopy field, a capsule type endoscope which is of a swallowable type is in practical use. The capsule type endoscope has an imaging function and a wireless communication function. Further, after the capsule type endoscope is introduced from a mouth of a subject for observation (inspection), it sequentially performs imaging while moving in an organ, e.g., a stomach or a small intestine in accordance with its peristaltic motion until it is naturally excreted, thereby acquiring information of the inside of the subject.

Subject internal information (image data) obtained in a body while the capsule type endoscope moves in a body cavity is sequentially transmitted to the outside based on wireless communication, and stored in an external provided memory. When the subject takes along a receiver including a wireless communication function and a memory function, he/she can freely move after swallowing the capsule type endoscope until the capsule type endoscope is excreted.

Furthermore, as one of wireless communication modes in the capsule type endoscope, a human body communication mode of utilizing a subject as a signal transmission medium to transmit image data to the outside has been proposed. For example, in JP-A 2006-513670 (KOKAI), two signal electrodes are provided on the outer peripheral surface of a capsule type endoscope, and a potential difference according to image data is produced between the two electrodes to cause a current to flow through a subject. Moreover, when the amount of current flowing between the receiving electrodes of an external receiving device arranged outside the subject is detected, the image data can be transmitted by utilizing the human body as a signal transmission medium.

Here, the capsule type endoscope disclosed in JP-A 2006-513670 has a configuration where transmitting electrodes are arranged on the outer surface, contact states of the transmitting electrodes of the capsule type endoscope put in the subject vary when moving in the subject. As a result, the impedance between the transmitting electrodes used to transmit a transmission signal of the capsule type endoscope also varies in the subject. Therefore, impedance mismatch between the transmitting electrodes and the subject occurs with respect to a change in the impedance between the electrodes, and a loss of a transmission signal power of the capsule type endoscope may possibly occur.

On the other hand, in JP-A 2006-513670 (KOKAI), a control method with respect to a change in the impedance between the transmitting electrodes is not explained in particular, and the loss of transmission signal power readily leads to a reduction in a reception signal level. Therefore, the reception signal is easily affected by noise, and stability of communication as a capsule type endoscopic system is apt to be degraded.

BRIEF SUMMARY OF THE INVENTION

It is an object of the present invention to provide a capsule type endoscope which can reduce the transmission signal power loss and stably perform communication.

According to a first aspect of the present invention, there is provided a capsule type endoscope which is introduced into a subject to acquire subject internal information and transmits the acquired subject internal information to the outside through the subject, comprising: a plurality of electrodes arranged on an outer peripheral surface of the capsule type endoscope; an electrode selecting section which selects two electrodes with a small transmission power loss from the plurality of electrodes as transmitting electrodes which are utilized to transmit the subject internal information; and a transmitting section which uses the two transmitting electrodes selected by the electrode selecting section to transmit the subject internal information to the outside of the subject.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5 is a view showing an example of a specific structure of an impedance measurement circuit.

DETAILED DESCRIPTION OF THE INVENTION

An embodiment according to the present invention will now be explained hereinafter with reference to the accompanying drawings.

Figure 1:
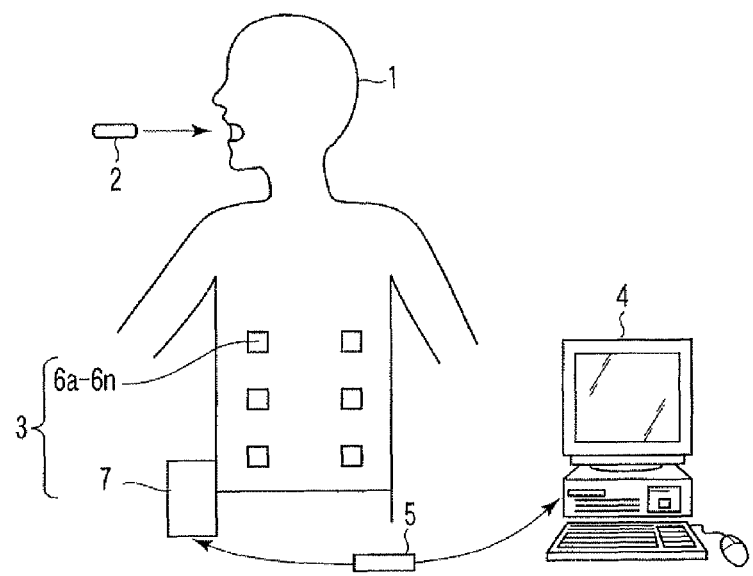
FIG. 1 is a schematic view showing the entire structure of a capsule type endoscopic system using a capsule type endoscope according to an embodiment of the present invention.

FIG. 1 is a schematic view showing the entire structure of a capsule type endoscopic system using a capsule type endoscope according to an embodiment of the present invention. The capsule type endoscopic system depicted in FIG. 1 includes a capsule type endoscope 2, a receiving device 3, a display device 4, and a portable recording medium 5.

The capsule type endoscope 2 is introduced into a subject 1, repeatedly performs imaging while moving in the subject 1 to acquire subject internal information (e.g., image data of the inside of the subject 1). Further, the capsule type endoscope 2 transmits a predetermined signal including the acquired subject internal information to the receiving device 3.

The receiving device 3 receives the transmission signal from the capsule type endoscope 2, and derives an image from the received signal. As shown in FIG. 1, the receiving device 3 includes receiving electrodes 6a to 6n and a processing device 7. The receiving electrodes 6a to 6n are electrodes that are arranged on the outer surface of the subject 1 to receive the transmission signal from the capsule type endoscope 2. The processing device 7 derives an image of the inside of the subject 1 from reception signals from the receiving electrodes 6a to 6n.

The display device 4 displays, e.g., the image of the inside of the subject 1 obtained by the capsule type endoscope 2. The display device 4 is configured as, e.g., a work station that displays an image based on data acquired by the portable recording medium 5. More specifically, the display device 4 has a function of reproducing a video signal from data recorded in the portable recording medium 5 and displaying the reproduced signal in, e.g., a CRT display or a liquid crystal display.

The portable recording medium 5 can be attached to/detached from the processing device 7 and the display device 4, and has a structure enabling outputting and recording information when attached to both the devices. Specifically, the portable recording medium 5 is attached to the processing device 7 to record the subject internal information of the capsule type endoscope 2 while the capsule type endoscope 2 is moving in a body cavity of the subject 1. Moreover, after the capsule type endoscope 2 is discharged from the subject 1, the portable recording medium 5 is removed from the processing device 7 and then attached to the display device 4, and the display device 4 reads the subject internal information recorded in the portable recording medium 5. When data is received/transmitted between the processing device 7 and the display device 4 through the portable recording medium 5, the subject 1 can freely move even if the capsule type endoscope 2 is moving in the subject 1, which differs from a case where the processing device 7 is connected with the display device 4 through a cable.

Figure 2:
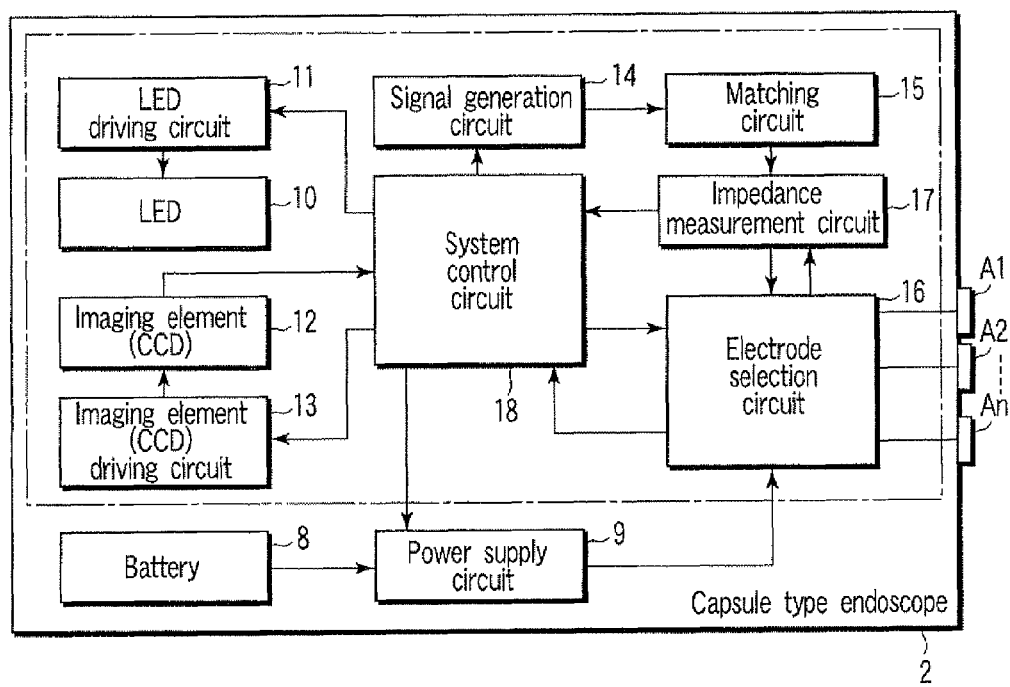
FIG. 2 is a block diagram showing a detailed structure of the inside of the capsule type endoscope.

FIG. 2 is a block diagram showing a detailed structure of the inside of the capsule type endoscope 2. That is, the capsule type endoscope 2 has a battery 8, a power supply circuit 9, an LED 10, an LED driving circuit 11, an imaging element (CCD) 12, an imaging element driving circuit 13, a signal generation circuit 14, a matching circuit 15, an electrode selection circuit 16, an impedance measurement circuit 17, a system control circuit 18, and transmitting electrodes A1 to An.

The battery 8 is a power supply for the capsule type endoscope 2. The power supply circuit 9 produces power from the battery 8, and supplies the power to each constituent element in the capsule type endoscope 2. Each constituent element in the capsule type endoscope 2 operates by using the power supplied from the power supply circuit 9 as a driving energy.

The LED 10 is a light source that illuminates an imaging region in the subject 1 when imaging the inside of the subject 1. The LED driving circuit 11 is a driving circuit that drives the LED 10. The imaging element 12 is a CCD imaging element that images a reflected light image from the imaging region illuminated by the LED 10 to acquire an image signal. The imaging element driving circuit 13 is a driving circuit that drives the imaging element 12. The image signal acquired by the imaging element 12 is digitized by the system control circuit 15, thereby generating image data of the inside of the subject 1.

Here, the LED and the CCD imaging element do not have to be necessary used as the light source and the imaging element. For example, a CMOS imaging element may be used as the imaging element.

Additionally, the capsule type endoscope 2 has a function as a transmitting section that converts the image data obtained by the system control circuit 18 into a predetermined transmission signal and stably transmits the signal to the receiving device 3 through the subject 1.

The signal generation circuit 14 constituting the transmitting section performs processing, e.g., modulation with respect to the image data of the subject 1 acquired by the system control circuit is, and generates a transmission signal that is used to transmit image data to the receiving device 3.

The matching circuit 15 changes the characteristic is impedance of the transmission signal generated by the signal generation circuit 14 to perform impedance matching between the transmitting electrodes A1 to An and the subject 1. Specifically, the matching circuit 15 includes a structure of varying the impedance of a capacitor component, an inductor component, or a resistor component to change the characteristic impedance of the transmission signal therein. In order to realize this structure, a structure where an impedance varying element is interposed between the transmitting electrodes A1 to An in series or in parallel can be adopted as the matching circuit 15. Using such a matching circuit 15 enables changing characteristics, e.g., the characteristic impedance of the transmission signal, a power of the transmission signal, a phase of the transmission signal, or a frequency of the transmission signal.

Additionally, the matching circuit 15 includes a current protection resistance element that specifies the maximum value of the current flowing in the subject 1.

The electrode selection circuit 16 supplies the transmission signal matched by the matching circuit 15 to two electrodes selected from the transmitting electrodes A1 to An. Specifically, the electrode selection circuit 16 selects two transmitting electrodes based on a voltage control signal from the system control circuit 18, and supplies the transmission signal to the selected transmitting electrodes. The operation of the electrode selection circuit 16 will be explained later in detail.

The transmitting electrodes A1 to An are electrodes that are used to transmit the transmission signal output from the matching circuit 15 to the inside of the subject 1. Each of the transmitting electrodes A1 to An has electroconductive properties, is formed of a metal that is superior in corrosion resistance and harmless to the human body, and arranged on the outer peripheral surface of the capsule type endoscope 2. It is to be noted that n means the number of electrodes set as required and it is an integer equal to or greater than 2.

The impedance measurement circuit 17 measures the impedance between two arbitrary transmitting electrodes, and outputs the measured impedance to the system control circuit 18.

The system control circuit 18 controls operations of the LED driving circuit 11, the imaging element driving circuit 13, the signal generation circuit 14, the matching circuit 15, the electrode selection circuit 16, and the power supply circuit 9, and generates image data of the subject 1 from an image signal obtained by the imaging element 12.

Figure 3:
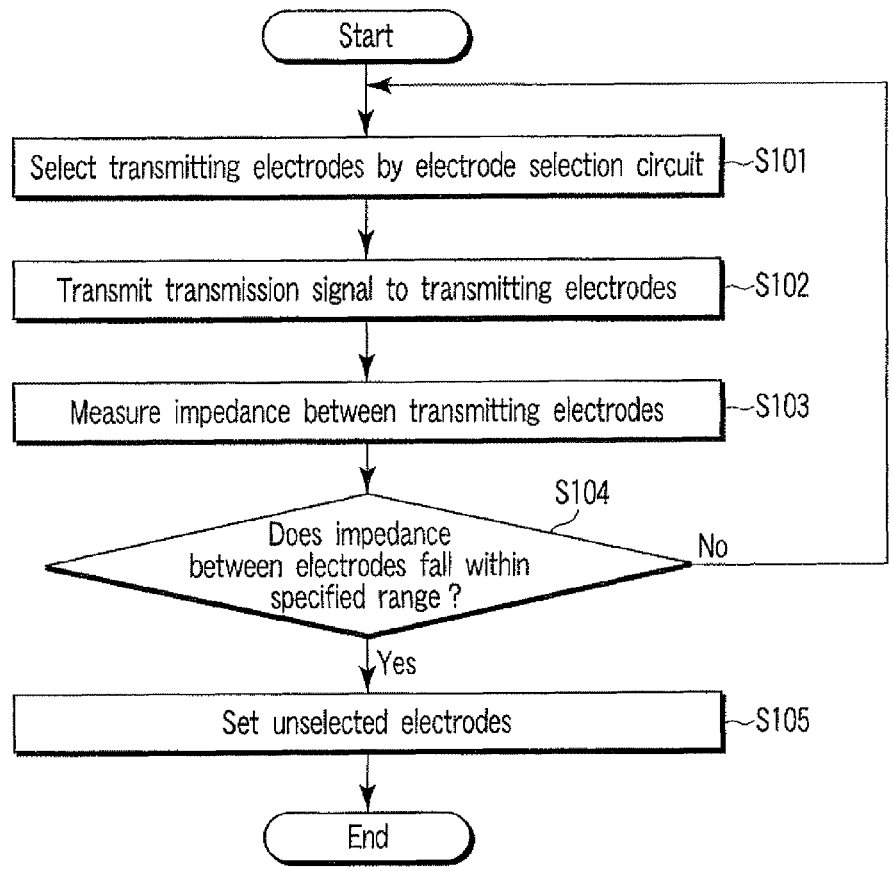
FIG. 3 is a flowchart showing feedback control concerning a transmission signal electrode selection method which reduces a transmission signal power loss between transmitting electrodes of the capsule type endoscope and a subject.

FIG. 3 is a flowchart showing feedback control concerning a transmission signal electrode selection method that reduces a transmission signal power loss between the transmitting electrodes of the capsule type endoscope 2 and the subject 1.

Prior to transmitting the transmission signal, the system control circuit 18 determines transmitting electrodes required to transmit the transmission signal (step S101). That is, the system control circuit 18 transmits a voltage control signal to the electrode selection circuit 16, and the electrode selection circuit 16 receives this signal to select two electrodes from the transmitting electrodes A1 to An. At the first time, arbitrary two transmitting electrodes can be selected.

After the transmitting electrodes are determined, the system control circuit 18 executes processing of transmitting the transmission signal to the selected two transmitting electrodes (step S102). That is, image data obtained by the imaging element 12 is transmitted to the signal generation circuit 14, and the signal generation circuit 14 performs processing, e.g., modulation to generate a transmitting signal. The matching circuit 15 carries out impedance matching, and then the transmission signal generated by the signal generation circuit 14 is supplied to the two transmitting electrodes selected in step S101.

Subsequently, the impedance measurement circuit 17 measures the impedance between the two transmitting electrodes used to transmit the transmission signal (step S103). That is, the impedance measurement circuit 17 utilizes the transmission signal to measure the impedance between the two transmitting electrodes when the transmission signal is supplied to the two electrodes in step S102, and outputs the measured impedance to the system control circuit 18.

Upon receiving the impedance from the impedance measurement circuit 17, the system control circuit 18 judges whether the received impedance falls within a specified range enabling efficient transmission of the transmission signal (step S104). For example, in the capsule type endoscope 2 having the plurality of electrodes arranged on the outer peripheral surface thereof, the impedance between the two selected electrodes becomes high and transmission power loss is increased when both the selected electrodes are not in contact with the human body. Further, the impedance between the two electrodes when both the electrodes are in contact with the human body becomes lower than that when they are not in contact with the human body, and transmission power loss is thereby decreased. However, when the impedance is too low, the efficiency of communication is degraded. Therefore, utilizing the impedance as a reference for a judgment on electrode selection enables judging a combination of two electrodes which can efficiently perform communication with a small transmission signal loss even though contact states of the transmitting electrodes vary when the capsule type endoscope is moving in the subject.

If it is determined that the impedance between the electrodes does not fall within the specified range as a result of the judgment in step S104, the control returns to step S101, and the system control circuit 18 outputs a voltage control signal to select another combination. Then, the processing in step S102 and subsequent steps is restarted. On the other hand, if it is determined that the impedance between the electrodes falls within the specified range as a result of the judgment in step S104, the system control circuit 18 and the electrode selection circuit 16 set unselected electrodes (step S105). In regard to the setting of unselected electrodes, it is preferable to pull down (reduce to a predetermined low potential) or pull up (increase to a predetermined high potential) potentials of unselected electrodes other than the two transmitting electrodes selected by the electrode selection circuit 16, for example. It is sufficient to effect such a setting by outputting a control signal to the electrode selection circuit 16 from the system control circuit 18. When a potential of each unselected electrode is set to a fixed potential, a possibility that each unselected electrode affects the transmission signal supplied from the currently selected two transmitting electrodes can be reduced.

FIGS. 4A to 4D are views showing examples of the transmitting electrodes A1 to An arranged on the outer peripheral surface of the capsule type endoscope 2.

Figure 4A:
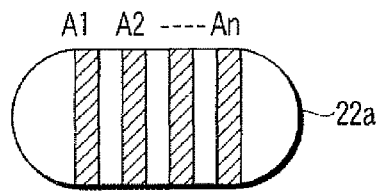
FIGS. 4A, 4B, 4C, and 4D are views showing examples of transmitting electrodes A1 to An arranged on the outer peripheral surface of the capsule type endoscope.
Figure 4C:
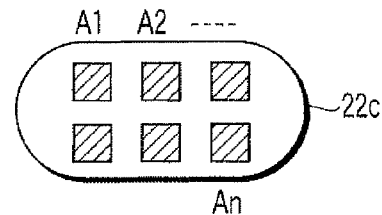
Figure 4B:
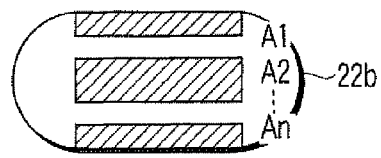
Figure 4D:
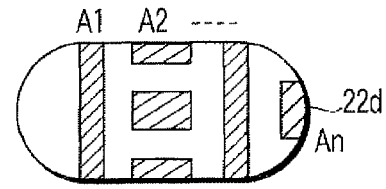

In a capsule type endoscope 22a depicted in FIG. 4A, ring-shaped transmitting electrodes A1 to An are arranged vertically with respect to the long-axis direction of the capsule type endoscope in such a manner that electrode intervals become equal to each other. Furthermore, in a capsule type endoscope 22b depicted in FIG. 4B, rectangular transmitting electrodes A1 to An are arranged horizontally with respect to the long-axis direction of the capsule type endoscope in such a manner that electrode intervals become equal to each other. Moreover, in a capsule type endoscope 22c depicted in FIG. 4C, square transmitting electrodes A1 to An are arranged in a reticular pattern on the outer peripheral surface of the capsule type endoscope. Additionally, in the capsule type endoscope 22d depicted in FIG. 4D, transmitting electrodes A1 to An are constituted of ring-shaped transmitting electrodes arranged vertically with respect to the long-axis direction of the capsule type endoscope, rectangular transmitting electrodes arranged horizontally with respect to the long-axis direction of the capsule type endoscope, and a transmitting electrode arranged at a dome-shaped portion of the capsule type endoscope.

According to the structures depicted in FIGS. 4A to 4D, the possibility that the transmitting electrodes A1 to An of the capsule type endoscope 2 come into contact with the subject is improved. Such structures, as well as the function of the electrode selection circuit 16, can suppress fluctuation in impedance between the transmitting electrodes.

It is to be noted that shapes or sizes of the transmitting electrodes are not restricted to those depicted in FIGS. 4A to 4D, and the transmitting electrodes can be arranged with arbitrary shapes and arbitrary sizes on the outer peripheral surface of the capsule type endoscope 2.

FIG. 5 is a view showing an example of a specific structure of the impedance measurement circuit 17. As explained above, the transmission signal supplied from the capsule type endoscope 2 to the receiving device 3 outside the subject is transmitted through the impedance measurement circuit 17 and fed to the two transmitting electrodes selected by the electrode selection circuit 16. Here, when the voltage control signal is received from the system control circuit 18, the electrode selection circuit 16 switches connection of the transmitting electrodes A1 to An in such a manner that a voltage according to the transmission signal from the impedance measurement circuit 17 is generated between the two transmitting electrodes. Specifically, as shown in FIG. 5, one of the two transmitting electrodes is connected with the impedance measurement circuit 17, and the other is connected with the ground.

Further, as shown in FIG. 5, the impedance measurement circuit 17 has a branch line coupler circuit 19, a driver circuit 20, and an analog-to-digital conversion circuit 21.

The branch line coupler circuit 19 distributes the transmission signal input from the matching circuit 15 to the two transmitting electrodes selected by the electrode selection circuit 16, and also distributes a reflection signal produced due to impedance mismatch of the two transmitting electrodes selected by the electrode selection circuit 16 and the inside of the subject to the system control circuit 18.

The driver circuit 20 amplifies the reflection signal distributed by the branch line coupler circuit 19 and outputs the amplified signal to the analog-to-digital conversion circuit 21. The analog-to-digital conversion circuit 21 converts the reflection signal output as an analog signal from the driver circuit 20 into a digital signal so that it can be processed by the system control circuit 18.

When such a structure as depicted in FIG. 5 is provided, signal intensity according to the absolute value of the impedance between the two transmitting electrodes can be detected. Furthermore, when the system control circuit 18 judges whether the impedance between the two transmitting electrodes matches with a threshold value of matching conditions, the operation of the electrode selection circuit 16 can be controlled.

Here, for example, a circulator circuit or a directional coupler circuit may be used in place of the branch line coupler circuit 19 in the impedance measurement circuit 17. Moreover, the branch line coupler circuit 19 can be configured by utilizing not only a lumped constant element but also a distributed constant element, e.g., a microstrip line. Additionally, as the impedance measurement method, a method utilizing an auto-balance bridge using an I-V converter may be adopted in place of the method utilizing the branch line coupler.

As explained above, according to this embodiment, even if contact states between the subject 1 and the transmitting electrodes A1 to An of the capsule type endoscope 2 that is led into and moves in the subject 1 vary and the output impedance is thereby changed, optimum electrodes can be selected from the plurality of transmitting electrodes arranged on the outer peripheral surface of the capsule type endoscope 2 to stably supply the transmission signal to the subject 1.

That is, when the contact states between the subject 1 and the transmitting electrodes arranged on the outer peripheral surface of the capsule type endoscope 2 vary, the electrodes are switched to other two electrodes that satisfy impedance conditions (i.e., the impedance falls within a specified range) of reducing transmission power loss due to impedance mismatch, and transmission is carried out with the switched electrodes. As a result, a state where the transmission power loss is reduced can be maintained, and the continuously stable transmission signal can be supplied to the subject.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule type endoscope which is introduced into a subject to acquire subject internal information and transmits the acquired subject internal information to the outside through the subject, comprising:
   a plurality of electrodes arranged on an outer peripheral surface of the capsule type endoscope;
   an impedance measuring section which measures an impedance between two electrodes among the plurality of electrodes;
   an electrode selecting section which selects two electrodes from the plurality of electrodes in accordance with the impedance measured by the impedance measuring section as transmitting electrodes which are utilized to transmit the subject internal information; and
   a transmitting section which uses the two transmitting electrodes selected by the electrode selecting section to transmit the subject internal information to the outside of the subject.

2. The capsule type endoscope according to claim 1, wherein the electrode selecting section further reduces potentials of unselected electrodes other than the two electrodes selected from the plurality of electrodes to a predetermined low potential or increases the same to a predetermined high potential.

3. The capsule type endoscope according to claim 1, wherein the electrode selection section selects the two electrodes based on a judgment of the received impedance output from the impedance measurement section, which judgment is performed by a system control section which judges whether the received impedance falls within a specified range enabling efficient transmission of the transmission signal.

* * * * *